US00PP35568P2

(12) United States Plant Patent
Ammerlaan

(10) Patent No.: US PP35,568 P2
(45) Date of Patent: Jan. 2, 2024

(54) ***CRASSULA* PLANT NAMED 'OVWOODS04'**

(50) Latin Name: *Crassula ovata*
Varietal Denomination: OVWOODS04

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/445,014

(22) Filed: Mar. 2, 2023

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Samuel R. McCoy, Jr.

(57) ABSTRACT

A new and distinct *Crassula* plant named 'OVWOODS04' which is characterized by the combination of a broad spreading growth habit, glossy succulent foliage, dark green that is longitudinally striped, blotched and marbled with a pale-yellow coloration, and the stability of all characteristics from generation to generation.

2 Drawing Sheets

Latin name of the genus and species: The Latin name of the genus and species of the novel variety disclosed herein is *Crassula ovata.*

Variety denomination: The inventive variety of *Crassula* disclosed herein has been given the variety denomination 'OVWOODS04'.

BACKGROUND OF THE INVENTION

Parentage: 'OVWOODS04' originated as a naturally occurring, whole-plant mutation of *Crassula* 'Crasmada' (Community Plant Variety Rights grant number 43697), a variety developed and owned by the inventor. The inventor of 'OVWOODS04' is a commercial ornamental plant producer and regularly discovers mutations of *Crassula* at his greenhouse operation in Bleiswijk, The Netherlands. For said mutations which seem to exhibit commercial potential, cuttings are taken to produce trial plants which are subsequently grown for evaluation. The variety now called 'OVWOODS04' was initially discovered in March of 2018 as a whole-plant mutation of 'Crasmada' which exhibited a large size and dark green, glaucous foliage borne on long lateral branches. At the time of discovery, cuttings were taken and the resulting plants were evaluated at the inventor's greenhouse. After further evaluation it was determined that the candidate's foliage characteristics would prove favorable for commercial marketability. The new variety was given the breeder denomination 'OVWOODS04'.

Asexual Reproduction: The variety now called 'OVWOODS04' was first asexually propagated by stem cuttings in March of 2018 at a greenhouse in Bleiswijk, The Netherlands and has since been vegetatively propagated through four additional generations. Through subsequent generations, the unique features of this cultivar are stable and reproduced true to type.

SUMMARY OF THE INVENTION

The cultivar 'OVWOODS04' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'OVWOODS04'. These characteristics in combination distinguish 'OVWOODS04' as a new and distinct *Crassula* cultivar:

1. *Crassula* 'OVWOODS04' exhibits a broad spreading to upright growth habit and an irregular broad obovate to globular profile; and
2. *Crassula* 'OVWOODS04' exhibits glossy succulent foliage; and
3. *Crassula* 'OVWOODS04' exhibits dark green foliage that is longitudinally blotched and marbled with a pale-yellow general coloration.

BOTANICAL DESCRIPTION OF THE PLANT

Figure 1:
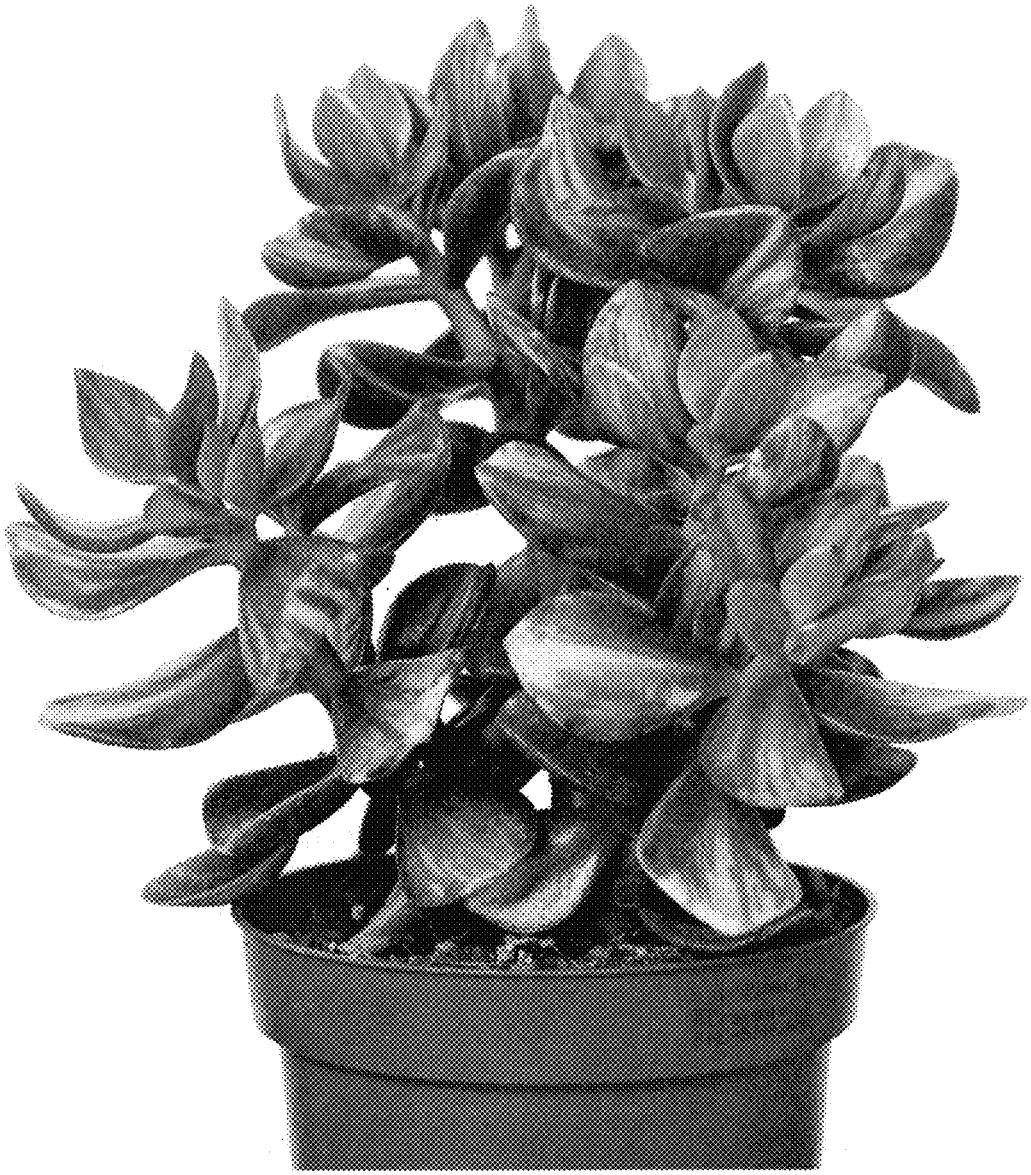
FIG. 1 illustrates, as nearly true as it is reasonably possible to make the same in color photographs of this type, an exemplary plant of 'OVWOODS04' grown in a commercial greenhouse in Heerhugowaard, The Netherlands. This plant is approximately 18 months old, shown planted in a 12 cm container.
Figure 2:
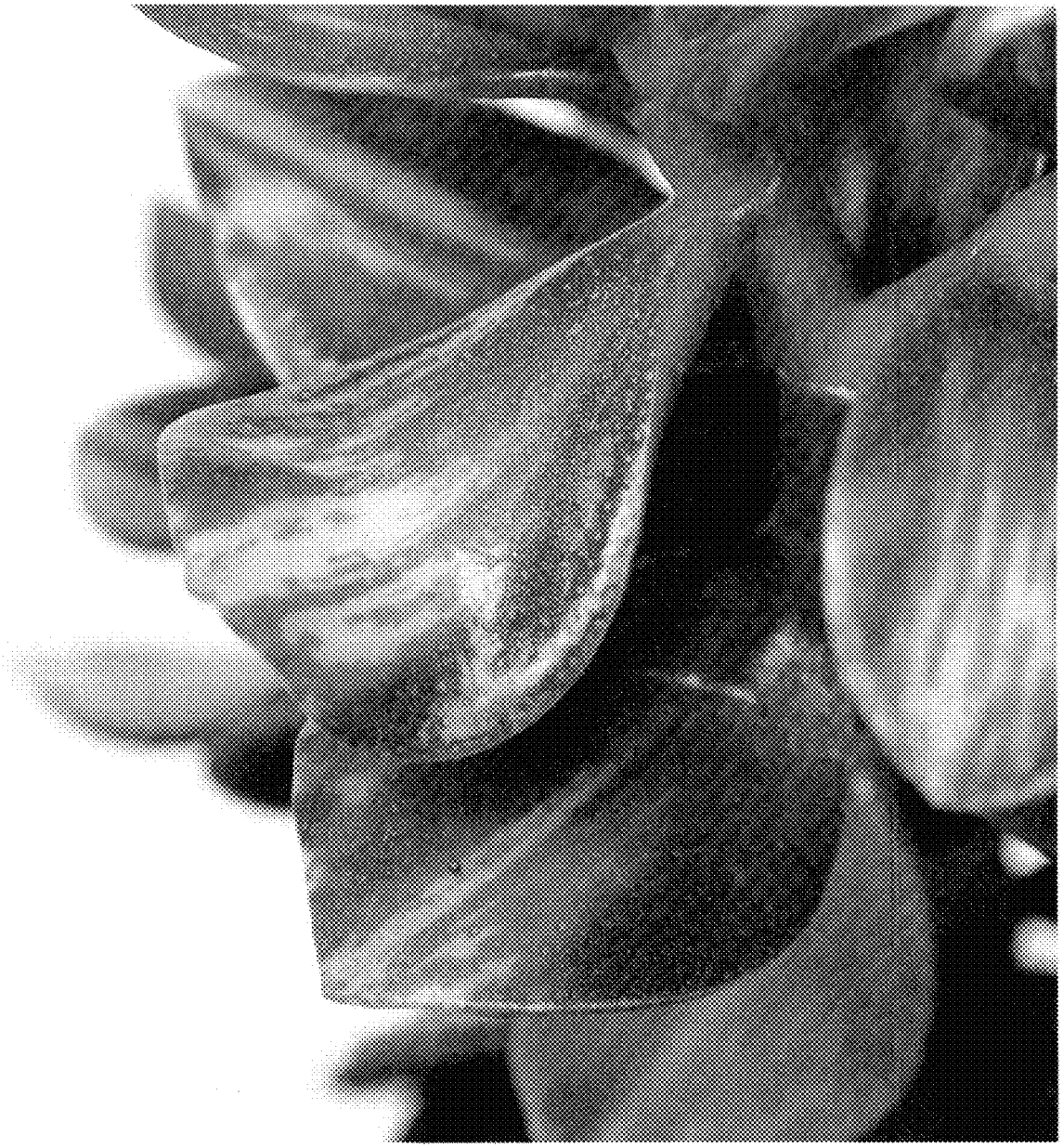
FIG. 2 illustrated, as nearly true as it is reasonably possible to make the same in color photographs of this type, the typical foliage of 'OVWOODS04'.

The following observations and measurements made in November of 2022 describe averages from a sample set of six specimens of 18-month-old 'OVWOODS04' plants grown in 12 cm nursery containers at commercial greenhouse in Bleiswijk, The Netherlands. The plants were grown in full sun to semi-shade. Plants were maintained with a standard fertility program for plants of this type and regularly watered with overhead irrigation as well as through use of ebb-and-flow hydroponic greenhouse benches. No chemical pest measures were taken.

Those skilled in the art will appreciate that certain characteristics will vary with older or, conversely, with younger plants. 'OVWOODS04' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'OVWOODS04' and comparisons with the parent and closest known commercial comparator are provided below.

Plant description:

*Growth habit.*—Broad spreading to upright perennial.

*Plant form.*—Irregular broad obovate to globular.

*Average height.*—17.9 cm from the soil level to the top of the foliar plane.

*Plant spread.*—Average of 21.1 cm.

*Plant vigor.*—Moderately vigorous.

*Propagation type.*—Stem cuttings.

*Time to initiate roots.*—Approximately 14 days to initiate roots at temperatures ranging from 15 to 20 degrees Celsius.

*Time to produce a rooted cutting.*—Approximately 6 weeks to produce a rooted cutting.

*Disease resistance.*—Neither resistance nor susceptibility to typical *Crassula* pests and diseases has been observed.

*Environmental tolerances.*—Adapt to, at least, USDA Zones 10 and 12 and temperatures as high as 40 degrees Celsius; low tolerance to rain; moderate to high tolerance to wind.

Root system:

*General.*—Moderately dense and freely branched rooting; roots are moderately fibrous.

*Distribution in the soil profile.*—Shallow to moderately deep.

*Diameter of roots.*—0.8 mm on average.

*Texture.*—Smooth and glabrous.

*Color.*—Greyed-orange, nearest to RHS 164A.

Stem:

*General branching habit.*—Multiple main stems, freely branching with lateral branches. Pinching isn't required but will improve branching.

*Main stems.*—Quantity of main stems per plant — 3. Attitude — Upright. Cross-section — Rounded. Texture — Glabrous; glaucous. Luster — Juvenile stems are very slightly glossy; mature stems are matte. Strength — Strong. Color, juvenile — Yellow-green, nearest to a mixture of RHS 147D and 148D. Color of the oldest wood — Grey-brown; nearest to RHS 199B and 199C.

*Lateral branches.*—Quantity of lateral branches — 7. Length of lateral branches — Approximately 5.7 cm. Diameter of lateral branches — Approximately 0.8 cm. Internode length — Approximately 1.7 cm. Attitude — At an average angle of 45 degrees to the main stem. Cross-section — Rounded. Texture — Glabrous; glaucous. Luster — Very slightly glossy. Strength — Strong. Color, juvenile — Yellow-green, nearest to a mixture of RHS 147D and 148D. Color, mature — Green, nearest to RHS 138A. Color at internodes — Green, nearest to RHS 138A.

Foliage:

*Phyllotaxy.*—Decussate.

*Division.*—Simple.

*Attachment.*—Sessile.

*Quantity.*—8 per lateral branch.

*Attitude.*—Upward.

*Lamina.*—Shape — Obovate to elliptic. Aspect — Longitudinally convex and lightly carinate; slightly to moderately curled upward, distally. Dimensions — 4.7 cm long and 3.2 cm wide. Thickness — Approximately 0.6 cm. Apex — Acute to broad, bluntly acute. Base — Narrowly cuneate. Margin — Entire; coarsely, not undulated to lightly undulated. Pubescence, texture and luster of the adaxial surface — Glabrous, smooth with glands present, and glossy. Pubescence, texture and luster of the abaxial surface — Glabrous, smooth with glands present, and glossy. Color — Juvenile foliage, adaxial surface — Green, nearest to a mixture of RHS 137A, 137B, NN137A and NN137D; longitudinally striped, blotched, and marbled with yellow-green, nearest to in between RHS 144A and 144B. The laminar glands are greyed-green, nearest to RHS N189B. Juvenile foliage, abaxial surface — Green, nearest to a mixture of RHS 137A and 137B; longitudinally striped, blotched, and marbled with yellow-green, nearest to in between RHS 144A and 144B. The laminar glands are greyed-green, nearest to RHS N189B. Mature foliage, adaxial surface — Nearest to a mixture of green and yellow-green, RHS NN137A, NN137B, 139A, and 147A; longitudinally striped, blotched, and marbled with a combination of yellow-green and greyed-green, particularly towards the apex, nearest to RHS 144A, 144B, 146A, 150D, and 160D. The laminar glands are greyed-green, nearest to RHS N189B. Mature foliage, abaxial surface — Nearest to a mixture of green and yellow-green, RHS 137A, 137B, NN137A, NN137B, 144A, and 144B; longitudinally striped, blotched, and marbled with a combination of yellow-green, green-white, and greyed-green, particularly towards the apex, nearest to RHS 150D, 157A, and 160D. The laminar glands are greyed-green, nearest to RHS N189B.

*Venation.*—No veins are visible.

Inflorescence: No flowering has been observed to date.

Comparison with the parent plant: Plants of the new cultivar 'OVWOODS04' differs from the parent, *Crassula* 'Crasmada' (U.S. Plant Pat. No. 28,426), in the following characteristics described in Table 1 below.

TABLE 1

| Characteristic | 'OVWOODS04' | 'Crasmada' |
|---|---|---|
| Growth habit. | Broad spreading to upright. | Broad upright. |
| Plant dimensions. | Shorter and broader than 'Crasmada'. | Taller and narrower than 'OVWOODS04'. |
| Foliage shape. | Broad obovate to elliptic. | Obovate. |
| General coloration of the foliage. | Dark green; striped, blotched, and marbled with pale-yellow, particularly towards the apex. | Solid dark green. |

Comparison with the closest known comparator: Plants of the new cultivar 'OVWOODS04' differ from the most similar variety known to the inventor, *Crassula* 'Minova Magic' (unpatented in the United States; Community Plant Breeder's Rights number EU37471), in the following characteristics described in Table 2 below.

TABLE 2

| Characteristic | 'OVWOODS04' | 'Minova Magic' |
|---|---|---|
| Plant size. | Larger than 'Minova Magic' | Smaller than 'OVWOODS04'. |
| Foliage size. | Larger than 'Minova Magic' | Smaller than 'OVWOODS04'. |
| Foliage aspect. | Longitudinally convex and lightly carinate; slightly to moderately curled upward, distally. | Flat. |
| General coloration of the foliage. | Darker green; striped, blotched, and marbled with a pale-yellow, particularly towards the apex. | Light to medium green. |
| Foliage luster. | Less glossy than 'Minova Magic'. | Glossier than 'OVWOODS04'. |

That which is claimed is:

1. A new and distinct variety of *Crassula* plant named 'OVWOODS04', substantially as described and illustrated herein.

* * * * *